US010117769B2

(12) United States Patent
Humphrey

(10) Patent No.: US 10,117,769 B2
(45) Date of Patent: Nov. 6, 2018

(54) ORTHOPEDIC KNEE BRACE

(71) Applicant: Jay C. Humphrey, Carnegie, PA (US)

(72) Inventor: Jay C. Humphrey, Carnegie, PA (US)

( * ) Notice: Subject to any disclaimer, the term of this patent is extended or adjusted under 35 U.S.C. 154(b) by 111 days.

(21) Appl. No.: 15/252,340

(22) Filed: Aug. 31, 2016

(65) Prior Publication Data
US 2018/0055673 A1 Mar. 1, 2018

(51) Int. Cl.
*A61F 5/01* (2006.01)

(52) U.S. Cl.
CPC .... *A61F 5/0125* (2013.01); *A61F 2005/0167* (2013.01); *A61F 2005/0197* (2013.01)

(58) Field of Classification Search
CPC .................. A61F 5/0125; A61F 2005/0197
See application file for complete search history.

(56) References Cited

U.S. PATENT DOCUMENTS

| | | |
|---|---|---|
| 1,510,408 A | 9/1924 | Lychou |
| 3,928,872 A | 12/1975 | Johnson |
| 4,408,600 A | 10/1983 | Davis |
| 4,489,718 A | 12/1984 | Martin |
| 4,565,190 A * | 1/1986 | Pirmantgen ........... A61F 5/0125 602/16 |
| 4,637,382 A | 12/1987 | Walker |
| 4,781,180 A | 11/1988 | Solomonow |
| 5,009,223 A | 4/1991 | Defonce |
| 5,399,149 A | 3/1995 | Frankowiak |
| 5,409,449 A | 4/1995 | Nebolon |
| 5,630,791 A | 5/1997 | Glynn |
| 6,409,693 B1 | 6/2002 | Brannigan |
| 6,540,709 B1 | 4/2003 | Smits |
| 6,691,434 B1 | 2/2004 | Couturier |
| 6,746,248 B2 | 6/2004 | Eastwood |
| 6,793,641 B2 | 9/2004 | Freeman et al. |
| 6,878,126 B2 | 4/2005 | Nelson et al. |
| 6,936,020 B2 | 8/2005 | Davis |
| 7,150,721 B2 | 12/2006 | Houser |
| 7,235,058 B2 | 6/2007 | Doty et al. |
| 7,410,472 B2 | 8/2008 | Yakimovich et al. |
| 7,462,160 B2 | 12/2008 | Nobbe et al. |
| 7,517,330 B2 | 4/2009 | Deharde et al. |
| 7,553,289 B2 | 6/2009 | Cadichon |
| 7,686,776 B2 | 4/2010 | Castillo et al. |
| 7,704,218 B2 | 4/2010 | Einarsson et al. |
| 7,833,181 B2 | 11/2010 | Cormier et al. |
| 7,846,115 B2 | 11/2010 | Seligman et al. |
| 7,927,299 B2 | 4/2011 | Krause |
| 7,947,004 B2 | 5/2011 | Kazerooni et al. |
| 8,257,293 B2 | 9/2012 | Ingimundarsen et al. |
| 8,282,588 B2 | 10/2012 | Ingimundarsen et al. |

(Continued)

*Primary Examiner* — Daniel J Colilla
(74) *Attorney, Agent, or Firm* — Gary P. Topolosky

(57) ABSTRACT

An apparatus that includes a composite fuselage and motion control system designed to protect the human leg from knee pain and muscular fatigue created by repetitive vertical movement or extended periods of squatting. Fuselage panels and frame encapsulate the leg and functionally integrate with hard shell boots to create a rigid exoskeleton structure that resists radial displacement of the knee or ankle. The fuselage 'open clamshell' leg harness utilizes wide composite body panels that disperse pressure across a large surface area, allowing the harness to provide body mass support and device securement without restriction of the body's circulatory system.

4 Claims, 4 Drawing Sheets

(56) References Cited

U.S. PATENT DOCUMENTS

| | | | |
|---|---|---|---|
| 8,425,441 | B2 | 4/2013 | Ingimundarsen et al. |
| 8,435,202 | B2 | 5/2013 | Lartonoix |
| 8,740,829 | B2 | 6/2014 | Lee et al. |
| 2001/0056251 | A1 | 8/2001 | Van Dyke et al. |
| 2003/0032907 | A1 | 2/2003 | Prahl |
| 2006/0167396 | A1 | 7/2006 | Berger |
| 2007/0232972 | A1 | 10/2007 | Martinez |
| 2008/0154165 | A1 | 6/2008 | Ashihara et al. |
| 2009/0198164 | A1 | 8/2009 | Krause |
| 2011/0071452 | A1* | 3/2011 | Auberger ............... A61F 5/0111 602/26 |
| 2013/0023800 | A1* | 1/2013 | Bedard ................ A61F 5/0123 600/595 |
| 2013/0038056 | A1 | 2/2013 | Donelin |
| 2014/0336554 | A1* | 11/2014 | Romo .................. A61F 5/0125 602/16 |
| 2016/0081839 | A1* | 3/2016 | Hassel ................. A61F 5/0113 602/28 |
| 2016/0374844 | A1* | 12/2016 | DeHarde ................ F16F 15/04 602/16 |

\* cited by examiner

ORTHOPEDIC KNEE BRACE

BACKGROUND OF INVENTION

This invention relates to orthopedic knee braces and, more specifically, to an apparatus that supports body mass and alleviates knee compartment stress through mechanical assistance. The present application consists of: a composite panel fuselage that encapsulates the leg; a motion control mechanism that supports body mass by managing flexion of the leg; and a lower support harness that integrates with hard shell boots. Main performance features of the present invention include enhanced impact protection, increased stabilization of the leg, mitigation of knee compartment stress and increased muscular efficiency.

Overuse, injury and age take their toll on a person's knees, degradation of cartilage and synovial fluid, known as Plica syndrome, is inevitable. Orthotic articulating (OA) knee braces that develop low levels of resistance to flexion have had some success in rehabilitation, preventive care and sports markets. However, more powerful systems capable of supporting body mass have been to date, ineffective from a commercial standpoint.

The present invention addresses ergonomic shortcomings of conventional orthotic knee braces by using a structured panel harness for securement of the knee brace to the leg. With rigid body panels instead of straps, the support harness of the present invention can focus or remove surface pressure on specific areas of the leg. With superior ergonomics and structural integrity, the fuselage of the present invention will comfortably support body mass without restricting the circulatory system of the user.

The following U.S. Patents, which describe orthotic braces of this general type, are incorporated by reference herein to establish the historic nature of such braces, and how and why such equipment is used: U.S. Pat. No. 1,510,408, entitled "Knee Brace"; U.S. Pat. No. 3,928,872, entitled "Leg support device for skiing"; U.S. Pat. No. 4,408,600, entitled "Leg aid device and method".

Performance advantages of the present invention are based on its ergonomic fuselage design with wide, rigid body panels of the upper and lower support harness encircling the leg, creating an 'open clamshell' structure that specifically avoids the femoral, tibial, genicular, saphenous and popliteal blood vessels of the leg. The open clamshell harness allows the present invention to develop pressure on the leg for securement and support without causing circulatory restriction.

This open clamshell design also addresses performance shortcomings of the prior art regarding orthotic knee braces. Conventional orthopedic knee braces still rely on bilateral frames and looping straps for securement of the device to the leg. When placed under structural load, conventional orthotic knee brace designs flex inward and the compression straps restrict circulation to the user's lower extremities.

The following U.S. Patents describe orthopedic style knee braces that have rigid support panels incorporated into their structure. U.S. Published Application No. 2007/0232972 has structural panel coverage of the posterior upper thigh and lower leg with strap securement system on front section of the leg. In comparison, the present invention uses a double panel 'open clamshell' structure for securement that disperses pressure across a larger area of the leg without restricting the inner thigh and inner calf regions.

U.S. Pat. No. 6,936,020, entitled "Orthopedic Splint" embodies the concept of rigid panels for securement. But panels of "Orthopedic Splint" have a dissimilar orientation than the present application and attach to a fixed position metal rod frame, making this patent example strictly a post-op treatment device.

The present invention differs from "Orthopedic Splint" in both construction and application. The composite panels overlap and attach to one other creating a strong, low profile fuselage that articulates with the leg during movement. That, in turn makes the fuselage design of the present invention feasible for a multitude of applications such as post-op rehab, sports orthotics and robotic assistance.

An example of a U.S. patent that uses a rigid leg harness for securement and support instead of looping straps would be U.S. Pat. No. 6,409,693, entitled "Leg Support Device". The leg collar in that example is an overlapping cuff that completely encircles the leg. In comparison to the ergonomic, low profile open clamshell design of the present invention, "Leg Support Device" still restricts blood flow and encroaches on the inner leg area. Advanced composite construction methods and the open clamshell design allow the present invention to achieve the similar assistance levels to that of "Leg Support Device" with better ergonomics and less structural Interference.

The following prior art describes an orthopedic leg brace with advanced composite frame construction; US Published Application No. 2013/0038056. This device, embodied in a commercial form by Bionic Power Llc., utilizes composite construction with a high level of panel coverage. The panels of this prior art example do not, however, represent the function of the present invention's 'open clamshell' support harness. Without rigid panels fixed to the main frame, US Published Application No. 2013/0038056 lacks the panel size, orientation and structural integrity needed to disperse mechanical pressure on the leg and support body mass.

Several prior art examples have broken free of the bilateral frame design by using a single outboard hinge for the frame. U.S. Pat. No. 8,740,829, entitled "Configurable sub-shell components in orthopedic devices", U.S. Pat. No. 7,704,218, entitled "Knee brace" and U.S. Pat. No. 5,009,223, entitled "Variable axis knee brace", are designs that have reduced structural interference with the inner leg. The three prior art examples, however, still encircle the leg with straps and do not function beyond what prior prophylactic knee braces are capable of. The present invention matches the inner leg profile of these prior art examples, with increased stability and structural integrity because of the innovative fuselage design.

The present invention employs a more effective motion control system when compared to prior art by using: a cam attached to the lower support harness; a roller bearing and leaf spring assembly attached to the upper support harness; and a common central pivot. This motion control system is drag-free, highly adjustable, compact and powerful. By moving a roller hearing over the cam profile to create mechanical pressure on the spring assembly, the present invention motion control device has nearly frictionless operation. Motion control system of the present invention has a smooth, responsive 'live' feeling, a performance trait repeatedly missed by prior art. Use of elastomeric straps, pneumatic springs, even other steel spring configurations found in examples of prior art are not capable of the smooth operation, radically increasing spring resistance or high rebound properties of the present invention's motion control system.

The following U.S. Patents describe orthopedic braces using spring resistance and motion control systems, are herein incorporated for reference. U.S. Pat. No. 5,399,149, entitled "Knee hinge with selectively limited motion". This prior art has the embodiment of a cam profile and spring deflection to create resistance.

Examples of motion control methods in a sports oriented knee brace would be U.S. Pat. No. 7,553,289, "Method, apparatus, and system for bracing a knee", and U.S. Published Application No. 2009/0198164. Also noteworthy is the commercially available example of hinges with flex resistance, i.e., the POD Active K8 with Human Hinge Technology.

In comparison to the present invention, prior art motion control systems are rudimentary, light duty designs with less adjustability and lower resistance levels. Prior art examples of motion control devices are designed to operate within the constraints of conventional knee brace structures. They cannot produce high levels of resistance without drastically reducing leg circulation. The present invention motion control system is more robust and powerful, being designed to work with the improved rigidity and fit of the 'open clamshell' support harness.

In addition to enhanced performance, the motion control system of the present invention is compact. When viewed from the exterior, the enclosed motion control system maintains the conventional profile of the leg, an important feature for consumers who want to experience mechanical assistance without looking mechanically assisted.

The following U.S. patent is example of a body mass support device that has evolved from robotics. U.S. Pat. No. 7,947,004, entitled "Lower extremity exoskeleton", relies on a cumbersome exterior frame and foot bed system for structure and alignment. In comparison to "Lower extremity exoskeleton", the present invention is sleek and simplistic, by making the upper and lower support harness structural components of the system, the present invention exists in form and function somewhere in between two pre-existing groups known as sports/orthopedic OA knee braces and robotic assistance. The present invention, listed as a 'Boorg'™, mixes the simplicity, fit and exterior profile of a sports oriented prophylactic knee brace, with the motion control capabilities of robotic assistance.

The orthopedic knee braces, ski aids, and robotic assistance devices described in the aforementioned incorporated patents are inferior to the present invention. In comparison to prior art, the present invention has an advanced fuselage that will not create circulatory restriction. It also has superior stability due to boot integration and a smooth, powerful method of motion control. The complete orthotic knee brace of this patent application is designed to fill the functional gap that exists between OA (orthotic-articulating) knee braces and robotic assistance systems.

It is an object of the present invention to provide an orthopedic knee brace that is worn to increase muscular efficiency and mitigate knee compartment stress, especially when deep squatting or holding a prolonged stance.

It is thus another object of the present invention to assist in its wearer/user in deep squatting or holding a prolonged stance through use of a motion control system attached to fuselage, primary components consisting of a cam, roller bearing, and leaf spring.

It is thus another object of the present invention to provide an orthopedic knee brace with ergonomic 'open clamshell' design that does not restrict the circulatory system of the lower body or deform under body mass supporting loads.

It is still another object of this invention to provide an orthopedic knee brace with modular fuselage construction that allows for anatomic customization.

It is yet another object to provide an orthopedic knee brace that functionally connects to hard shell boots creating a structure that can resist radial displacement of the knee and ankle.

From a functional standpoint, skiing aids have the most performance similarities to the present invention. In regards to commercial art, there are three established designs to mention:

CADS System—The latest rendition of CADS utilizes flexible carbon rods mounted to the back of a boot with the other end anchoring to the hip area by means of a posterior belt. The CADS motion control system is simple in function and operation. It is not a prophylactic system in the sense that coverage and leg stabilization is minimal. The flex rod motion control system has limited adjustability and the boot interface is rear mounted resulting in improper boot shell flex and loss of compliance between the lower leg and boot.

Ski Mojo—This system utilizes a rear facing boot mount similar to the CADS design, a semi-structured knee compartment, an upper thigh/posterior attachment, and a motion control system operated by extension spring. The Ski Mojo is not a rigid structure, so it has limited leg stabilization and prophylactic function. Compression strap thigh and posterior connection restricts circulation and does not enable truly independent leg support. Furthermore, Ski Mojo suffers from the same functional drawbacks of any rear facing boot-mounted design. The device will not retain the intended flex pattern of the boot.

Againer—A twin spar structure pivoting at the knee has a rigid rear facing frame member for leg stabilization and motion control with attachment to the boot being rear mounted. This system is the most robust and powerful of the three commercial designs with a unified structure from boot to thigh and a pneumatic spring for motion control. Unlike a Boorg 'open clamshell' design of this invention, the Againer structure encroaches on the inner leg profile causing interference between the medial thigh areas. The Againer design motion controller, being an exposed pneumatic piston, is also damage prone and lacks the adjustability and frictionless operation of a Boorg system. In addition, the Againer mounts to the boot shell in the same method as the previous ski aid designs.

The Boorg composite fuselage and panels have a high amount of coverage and structural rigidity. And the invention encapsulates and stabilizes the leg to a higher degree than anything previously listed. With addition of the motion control device, the Boorg becomes capable of isolating the knee compartment from damaging quadriceps tension and can even support body mass. While the above three commercial systems can also do body mass support, they cannot do so at the same level of performance as a Boorg motion control device. By using a roller bearing and cam for spring actuation, the present invention has a motion control system that is exceptionally smooth with a high degree of adjustability. Spring resistance of a Boorg motion control system can be increased, decreased, delayed, reversed or disengaged, thus allowing the user to customize performance to his/her specific needs and applications.

It is important to note that the features of the present invention; structural integrity, coverage, ergonomic design, boot integration and adjustable motion control give it the potential to represent many different things to many different people. A Boorg device can adapt to multiple applications while being both preventive and rehabilitative in purpose.

SUMMARY OF INVENTION

Accordingly, it is a principal object of this invention to provide an orthopedic knee brace fuselage with motion control system to mitigate stress on the knee compartment, protect the leg and support body mass.

It is another object herein to provide an orthopedic knee brace with a rigid 'open clamshell' harness structure that does not restrict blood circulation or deform under body mass supporting loads.

It is another object to utilize advanced composite construction methods including monocoque voids and directional layup patterns to create a low profile, lightweight orthotic knee brace fuselage capable of supporting body mass.

It is another object of this invention to attain customized fit through the use of modular fuselage sections that can be individually replaced or adjusted.

It is another object to use the open clamshell structure as a method of interface with a hard shell boot, allowing the two components to more effectively disperse and redistribute destructive internal and external forces.

It is another object to provide a motion control system that uses a roller bearing, leaf spring and cam design for adjustability and frictionless operation.

It is yet another object to provide a lower body exoskeleton that utilizes composite panels and the motion control system itself, as stressed members of the fuselage structure.

In accordance with the foregoing objects, and others which will become apparent hereinafter, there is provided a hinged motion control system operating in a central location beside the knee joint, attaching rotatably to an upper and lower support harness that follow the path of natural leg movement. By rotating a cam fixed to the lower support harness against a roller bearing and leaf spring attached to the upper support harness, spring deflection is created and utilized to control flexion or hyperextension of the leg through the rotatably attached, open clamshell support harness. Spring resistance of the present invention is used in conjunction with the rigid fuselage design to support body mass and reduce tension on the knee compartment. The present invention includes boot integration and a high level of body coverage to provide unmatched levels of protection and stability.

Other objects and advantages of the present invention will become apparent from the following descriptions, taken in connection with the accompanying drawings, wherein, by way of illustration and example, an embodiment of the present invention is disclosed.

BRIEF DESCRIPTION OF THE DRAWINGS

The drawings constitute a part of this specification and include representative embodiments that may be embodied in still other varying forms. It is to be understood that in some instances various aspects of the invention may be shown exaggerated or enlarged to facilitate an understanding of the invention. Corresponding reference characters indicate corresponding parts through several views.

The above mentioned and other features and advantages of this invention, and the manner of attaining them, will become more apparent and the invention will be better understood by the reference to the following descriptions of embodiments of the invention taken in conjunction with the accompanying drawings in which.

DETAILED DESCRIPTION OF PREFERRED EMBODIMENTS

Figure 1:
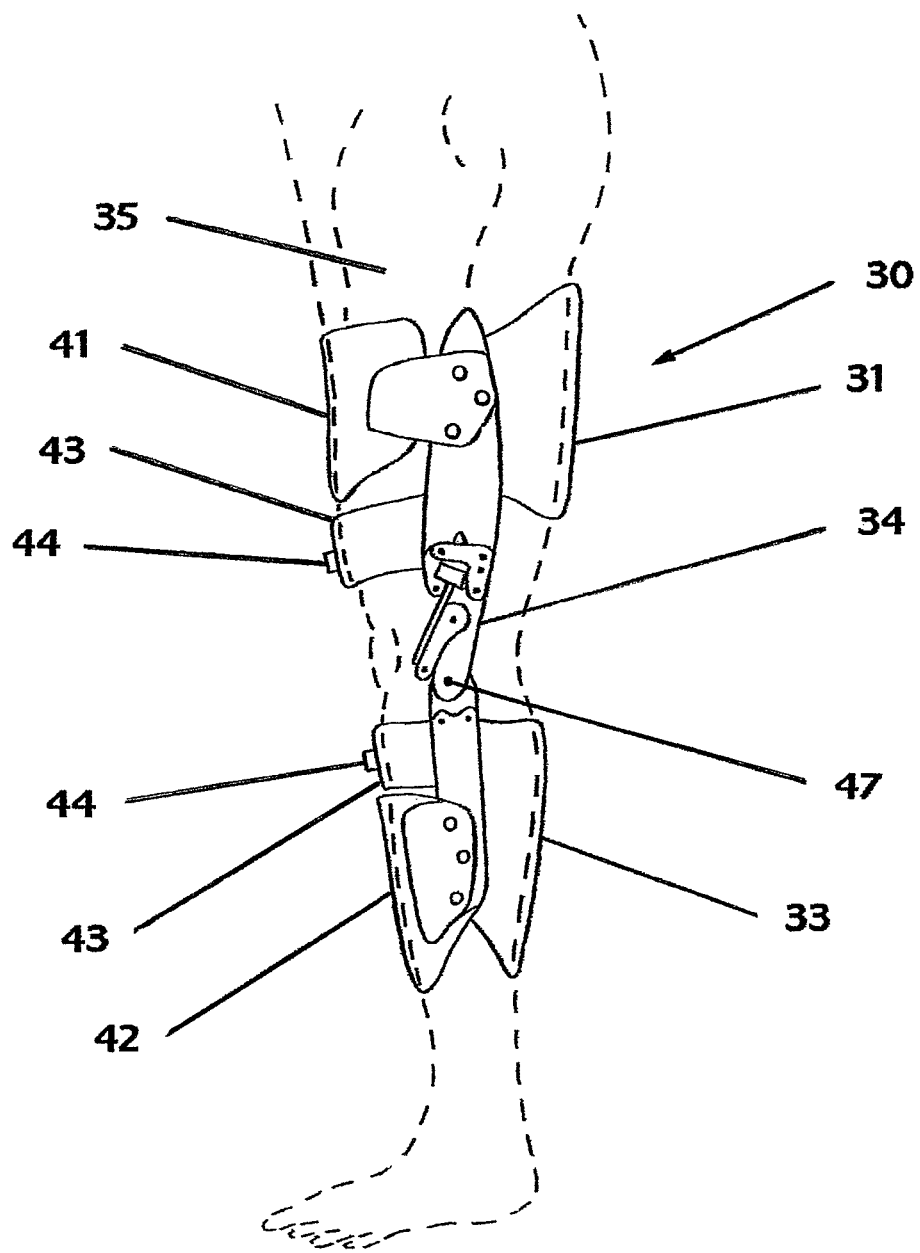
FIG. 1 is an outer side view of an adjustable orthopedic knee brace assembly having a motion control system and composite panel construction secured to a human leg.

Detailed descriptions of the preferred embodiments are provided herein. It is to be understood, however, that the present invention may be embodied in various forms.

Therefore, specific details disclosed herein are not to be interpreted as limiting, but rather as a basis for the claims and as a representative basis for teaching one skilled in the art to employ the present invention in virtually any appropriately detailed system, structure or manner.

While the invention has been described in connection with or more preferred embodiments, it is not intended to limit the scope of the invention to the particular form set forth. On the contrary, it is intended to cover such alternatives, modifications, and equivalents as may be included with the spirit and scope of the invention as defined by the appended claims.

Reference is now made specifically to the drawings in which identical or similar parts are designated by the same reference numerals throughout.

Referring to FIG. 1, an orthopedic knee brace 30 is shown operatively attached to a human leg 35 with a main pivot 47 and adjustable motion control system 34 disposed between the upper support harness 31 and the lower support harness 33. Orthopedic knee brace 30 is secured to the human leg 35 by the upper support harness 31 and the lower support harness 33. Turnbuckle control arm 40 (hidden) with turnbuckle locking mechanism 44 connects upper support harness front panel 41 and lower support harness front panel 42 to knee compartment frame 43. This turnbuckle arm feature enables fit adjustment and entry/exit of orthopedic knee brace 30.

Figure 2:
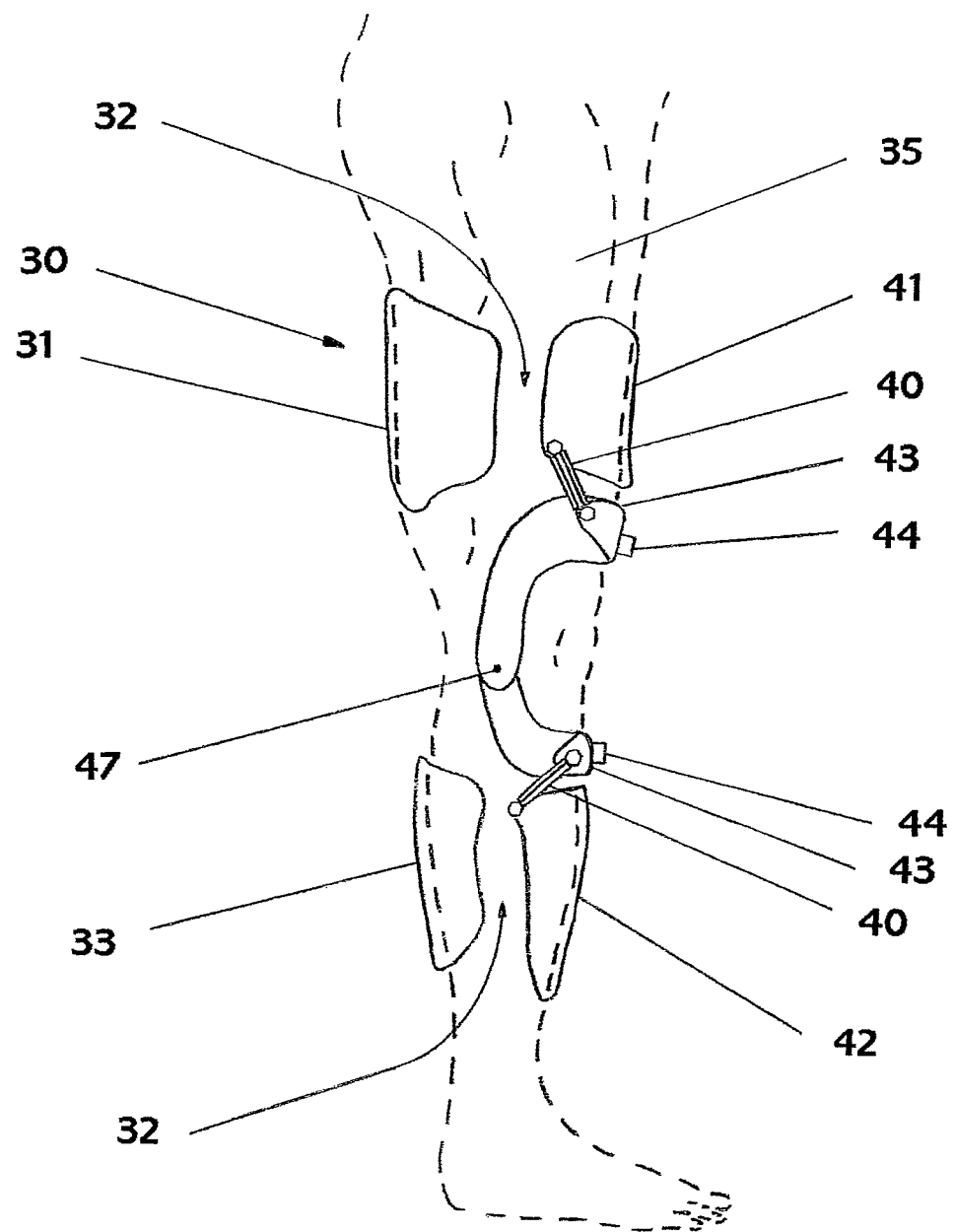
FIG. 2 is an inner side view of an adjustable orthopedic knee brace assembly with a structured 'open clamshell' fuselage secured to the human leg.

FIG. 2 is an inside view of an orthopedic knee brace 30 shown operatively attached to the human leg 35. This view shows rigid body panels of upper support harness 31 and lower support harness 33 encircling the leg to form an open clamshell structure with an ergonomic relief zone 32.

FIG. 2 further shows turnbuckle control arm 40 connected to upper support harness 31 and lower support harness 33. Turnbuckle control arm 40 when engaged, serves as a structural link from knee compartment frame 43 to upper support harness front panel 41 and lower support harness front panel 42. This design creates a rigid exoskeleton structure around the human leg 35 that articulates at a main pivot 47 located on each side of the knee's central axis.

Turnbuckle control arm 40, when released from knee compartment frame 43 by turnbuckle locking mechanism 44, enables upper support harness front panel 41 and lower support harness front panel 42 to pivot into an open position. This allows entry of human leg 35 into the orthopedic knee brace 30. When turnbuckle control arm 40 is engaged to knee compartment frame 43 thru turnbuckle locking mechanism 44, a rigid open clamshell structure with ergonomic relief zone 32 is created around the upper and lower leg. That open clamshell design provides three features that are objects of the present invention: impact protection for the leg, body mass support without circulatory restriction and functional integration between the fuselage and boot.

The open clamshell design with ergonomic relief zone 32 develops pressure on the human leg 35 without the side effects seen in conventional knee brace designs. The rigid upper support harness 31 and lower support harness 33 panels do not deform under load and distribute pressure evenly across large areas of the human leg 35. This allows the motion control system 34 (hidden) to create leg flexion or hyperextension resistance without creating discomfort or circulatory restriction.

Figure 3:
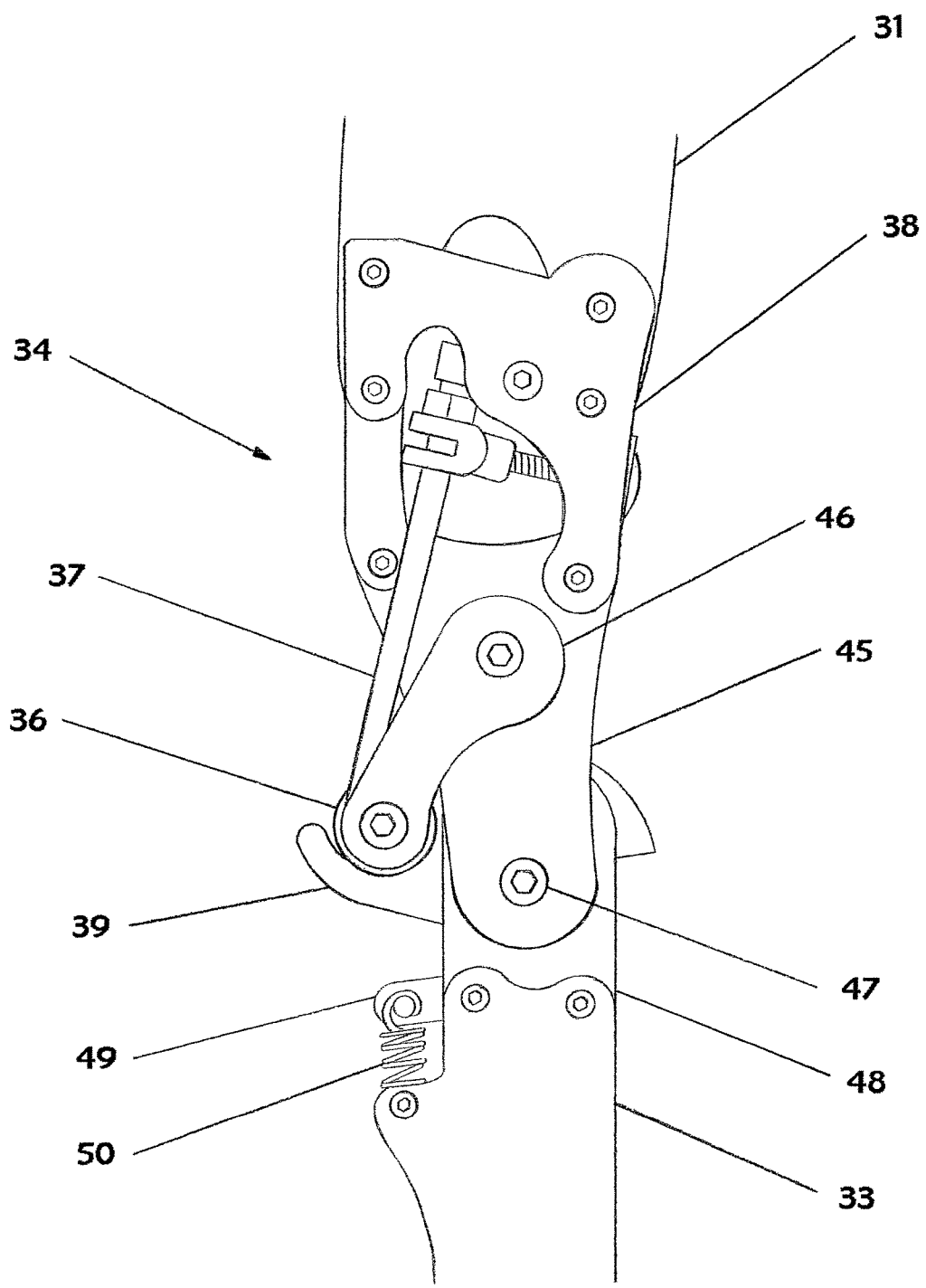
FIG. 3, consistent with FIG. 1, is the outer side view of the orthopedic motion control hinge with leaf spring harness, control arm and release mechanism that embodies principals of the present invention.

Referring to FIG. 3, a close up outside view of the adjustable motion control system 34 is shown with roller bearing 36 leaf spring 37 adjustable spring mount 38 and spring control arm 46 attached to upper pivot plate 45. The upper pivot plate 45 rotates on the main pivot 47 and serves as mounting point for upper support harness 31.

Cam 39, engagement latch 49 and engagement latch spring 50 are attached to the lower pivot plate 48 rotating independent of the upper pivot plate 45 at the main pivot 47. Lower pivot plate 48 also serves as mounting point for the lower support harness 33.

An adjustable motion control system 34 comprises: a roller bearing 36, a leaf spring 37 and an adjustable spring mount 38 attached to upper pivot plate 45. Roller bearing 36 of the upper pivot plate 45 assembly travels on the outer edge of cam 39 fixed to lower pivot plate 48 assembly. When the upper support harness 31 and lower support harness 33 move during flexion, the roller bearing 36 of motion control system 34 traces the cam 39 profile and moves the connected spring control arm 46, creating leaf spring 37 deflection. Leaf spring 37 pressure between the roller bearing and cam creates directional resistance that inhibits flexion or hyperextension of the motion control system 34, and by pairing that with the superior ergonomics of the open clamshell support harness, the present invention can support body mass and mitigate stress on the knee compartment during squatting and repetitive movement.

Performance of motion control system 34 is determined by the shape of cam 39, size of roller bearing 36, size and material choice of leaf spring 37 and the amount of preload on adjustable spring mount 38.

Figure 4:
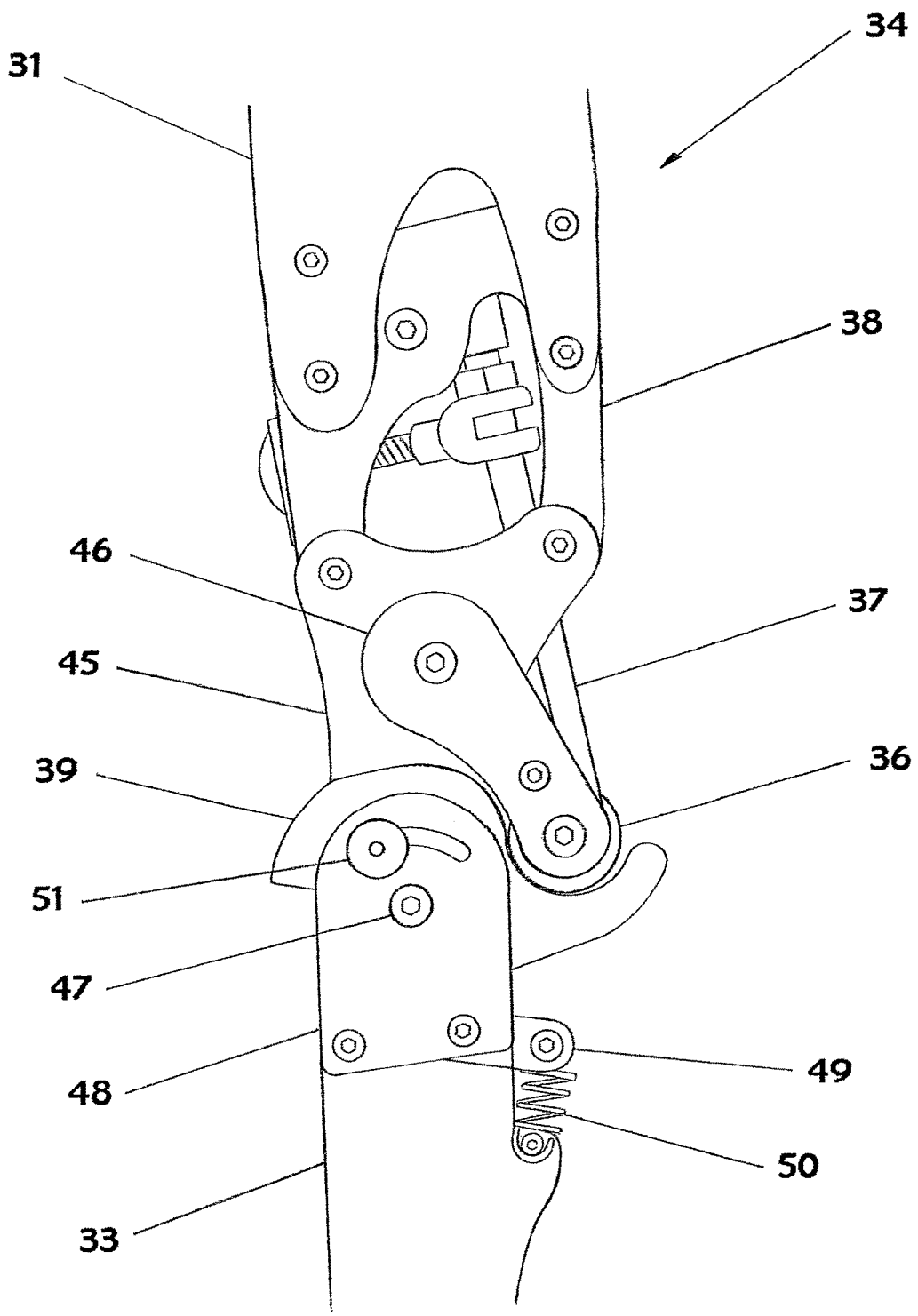
FIG. 4, consistent with FIG. 2, is the inner side view of the orthopedic motion control hinge with a cam and roller bearing mechanism.

Referring to FIG. 4, a close up inside view of the adjustable motion control system 34 is shown with roller bearing 36 leaf spring 37, adjustable spring mount 38 and spring control arm 46 attached to upper pivot plate 45. Upper pivot plate 45 rotates on the main pivot 47 and serves as mounting point for upper support harness 31.

Lower pivot plate 48, cam 39 and engagement latch 49 rotate on the main pivot 47 and serve as mounting point for the lower support harness 33. Engagement latch spring 50 keeps engagement latch 49 locked to cam 39 until manually pulled out of position.

Engagement latch 49 locks cam 39 to lower pivot plate 48 and lower support harness 33. When engagement latch 49 is pulled to an open position, cam 39 will rotate independent of lower pivot plate 48 and disengage leaf spring 37 resistance of the motion control system 34. Reengagement of cam 39 to engagement latch 49 occurs when cam 39 rotates counter-clockwise against the adjustable cam stop 51, allowing engagement latch spring 50 to pull engagement latch 49 back into a locked position with cam 39.

What is claimed is:

1. An orthopedic brace for the body comprising a motion control system attached to an upper and lower extremity harness divided by a pivotably mounted hinge mechanism, said orthopedic brace comprising:
    a. upper extremity harness support housing;
    b. a lower extremity harness support housing;
    c. an adjustable hinge mechanism connecting with a central pivot, between the upper extremity harness and the lower extremity harness; and
    d. said motion control system being built around the central pivot of the adjustable hinge mechanism, said motion control system connecting the upper extremity harness to the lower extremity harness,
        wherein the motion control system is used as a means for (i) mitigating stress on a human knee, (ii) supporting body mass; and (iii) increasing muscular efficiency, and
        wherein the motion control system comprises; a roller bearing, a control arm and a leaf spring attached to the upper extremity harness support housing, with motion control system rotating against a cam attached to lower extremity harness support housing during leg movement.

2. The orthopedic knee brace of claim 1 wherein the cam for the motion control system is replaceable for ease of adjustment.

3. The orthopedic knee brace of claim 1 wherein the motion control system functions as a common pivot and attachment point for the upper extremity harness support housing and the lower extremity harness support housing.

4. The orthopedic knee brace of claim 1 wherein the motion control system can induce, delay and reverse flexion resistance by manipulating at least one of:
    the cam shape, roller bearing size, and the leaf spring harness adjustment.

* * * * *